(12) United States Patent
Kuo et al.

(10) Patent No.: US 6,219,136 B1
(45) Date of Patent: Apr. 17, 2001

(54) DIGITAL SIGNAL PROCESSOR KNITTING SCANNER

(75) Inventors: C. C. Kuo, Bowling Green; Jimmy D. Claiborne, Scottsville; Henry L. Cantrell, Bowling Green; Steve T. Turner, Smith Grove; Glenn Wethington, Bowling Green, all of KY (US)

(73) Assignee: Union Underwear Company, Inc., Bowling Green, KY (US)

( * ) Notice: Subject to any disclaimer, the term of this patent is extended or adjusted under 35 U.S.C. 154(b) by 0 days.

(21) Appl. No.: 09/261,018

(22) Filed: Mar. 2, 1999

Related U.S. Application Data

(60) Provisional application No. 60/076,577, filed on Mar. 3, 1998.

(51) Int. Cl.[7] .................................................. G01N 21/00
(52) U.S. Cl. ............................................ 356/238.2; 66/157
(58) Field of Search .............................. 356/238.1, 238.2, 356/238.3, 429, 430, 431; 250/563, 562, 571, 572; 66/157, 166, 219

(56) References Cited

U.S. PATENT DOCUMENTS

| | | | |
|---|---|---|---|
| 2,919,624 | * | 1/1960 | Lindemann ........................ 356/238.1 |
| 3,065,615 | | 11/1962 | Abrams . |
| 3,139,911 | | 7/1964 | Breitmeier . |
| 3,193,688 | | 7/1965 | Morton et al. . |
| 3,303,698 | | 2/1967 | Loepfe . |
| 3,305,687 | | 2/1967 | Vinzelberg et al. . |
| 3,405,556 | | 10/1968 | Gonsalves et al. . |
| 3,584,225 | * | 6/1971 | Lindemann et al. .............. 356/238.2 |
| 3,589,816 | | 6/1971 | Sugaya . |
| 3,612,702 | | 10/1971 | Troll . |
| 3,655,989 | * | 4/1972 | Robinson ............................. 356/431 |
| 3,657,727 | | 4/1972 | Blevins . |
| 3,733,855 | * | 5/1973 | Bliss-Hill et al. ..................... 66/219 |
| 3,920,970 | | 11/1975 | Slaker . |
| 4,057,350 | | 11/1977 | Craig . |
| 4,057,351 | | 11/1977 | Fomenko . |
| 4,093,866 | | 6/1978 | Kasdan et al. . |
| 4,124,300 | | 11/1978 | Mead et al. . |
| 4,155,012 | | 5/1979 | Clarke et al. . |
| 4,260,899 | | 4/1981 | Baker . |
| 4,265,545 | | 5/1981 | Slaker . |
| 4,378,161 | | 3/1983 | Maddox . |
| 4,464,913 | * | 8/1984 | Rosenquist et al. .................. 66/166 |
| 4,610,707 | | 9/1986 | Grundy . |
| 4,748,334 | * | 5/1988 | Kobayashi et al. ................. 356/431 |
| 4,764,876 | | 8/1988 | Whitener, Jr. et al. . |
| 4,767,935 | | 8/1988 | Anderson et al. . |

(List continued on next page.)

*Primary Examiner*—Hoa Q. Pham
*Assistant Examiner*—Sang H. Nguyen
(74) *Attorney, Agent, or Firm*—John F. Salazar; Middleton Reutlinger

(57) ABSTRACT

A digital signal processor system is provided which detects defect in tubular knit fabric. The signal processor system is attached to a circular knitting machine or the like and utilizes a fiber optic scanning head for obtaining light reflectance data from the material. Fiber optic material is utilized to project light against the fabric web and another fiber optic bundle is utilized to read reflected light. A opto-sensor pixel array is utilized to provide voltage data to a digital signal processor which then analyzes the data to determine the existence of end out, holes, light or heavy yarn and needle run conditions.

18 Claims, 11 Drawing Sheets

U.S. PATENT DOCUMENTS

| | | |
|---|---|---|
| 4,788,442 | 11/1988 | Sabater et al. . |
| 4,868,403 | 9/1989 | Takahashi et al. . |
| 4,924,406 | 5/1990 | Bergamini et al. . |
| 4,952,062 | 8/1990 | Bean, III et al. . |
| 4,953,400 | 9/1990 | Bossuyt . |
| 4,972,091 | 11/1990 | Cielo et al. . |
| 4,984,896 | 1/1991 | Flamig . |
| 5,047,640 | 9/1991 | Brunnschweiler et al. . |
| 5,068,799 | 11/1991 | Jarrett, Jr. . |
| 5,157,266 | 10/1992 | Schmiedl . |
| 5,160,850 | 11/1992 | Spirig et al. . |
| 5,270,787 | 12/1993 | Shofner et al. . |
| 5,283,623 * | 2/1994 | Muhlberg et al. ................ 356/283.1 |
| 5,345,515 | 9/1994 | Nishi et al. . |
| 5,416,593 | 5/1995 | Vercruysse . |
| 5,420,439 * | 5/1995 | Landwehrkamp et al. ....... 356/238.1 |
| 5,467,194 * | 11/1995 | Pellinen et al. ..................... 356/429 |
| 5,499,794 | 3/1996 | Aeppli . |

* cited by examiner

DIGITAL SIGNAL PROCESSOR KNITTING SCANNER

This application claims the benefit of U.S. Provisional Application No. 60/076,577 filed Mar. 3, 1998.

BACKGROUND OF THE INVENTION

1. Field of the Invention

This invention relates to defect detection and inspection of knitted products utilizing light reflected off of the product, and more particularly, this invention is directed towards detection of defects in varying types of knitted products through the use of fiber optics and digital signal processors which reads reflected light.

2. Prior Art

Surface detection of light from optical components such as optical scanners and other such devices have been widely used in industry and in varying capacities. These detectors typically use electrical signals produced by an optical photo-sensor which may be digitized and processed as necessary in order to produce analytical data representing the scanned object. Most optical scanners use light emitted from a light source and an optical system in order to illuminate the object and focus a small area of light onto the illuminated object in combination with an optical photo-sensor. The most common type of photo-sensor device utilized in these systems is a charge coupled device or CCD. A CCD may comprise a large number of light sensitive cells or pixels each of which collects or accumulates electrical charges in response to the reflected light. Since the size of the accumulated electrical charge in any given cell or pixel is related to the intensity and duration of the light exposure, a CCD may be used to detect light and dark spots on a surface which reflects the focused light. In most photo sensing devices, the voltage of a CCD pixel is measured and discharged at regular time intervals in order to provide sampling intervals sufficient to characterized the object being analyzed and also to provide data which may be accumulated and digitized over a specified time period. However, application of such photo sensing devices has proved difficult in the area of defect detection and inspection of knitted products.

Inspection of knitted products has been very difficult to apply to photo optic devices due to the various styles of knitted products which may vary the thickness of the inspected material. Further, this analysis is made even more difficult due to the different types of defects which may occur in knitting machines. Finally, the style of yarn utilized in these knitting machines can significantly affect the data obtained from optical detection and subsequent analysis.

Of the types of fabric knitted by circular knitting machines, fleece, rib and jersey are the most common and consequently defect detection of all three materials is significantly desired. Fleece material is made up of a three yarns requiring a facing yarn, a tie-in yarn and a backing yarn. Fleece material may have up to four or five differing styles. There is additionally a two-end fleece fabric wherein only a facing and backing yarn are utilized. Of the most common three-end yarns, 18 yarn is utilized for the bigger and heavier material wherein 100% cotton content is desired. Additionally, 24 yarn and 28 yarn materials may be utilized for blended polyester and cotton fabrics.

There is additionally jersey style and rib construction style fabric wherein dual yarn or single yarn materials are utilized to produce a thinner fabric. In jersey material construction for use in tee shirts and the like, photo-optic characteristics will be significantly different as compared to both rib and fleece material.

Any defect detection and inspection system must have the ability to differentiate between these three types of material in order to "see" defects occurring in the fabric. These defects may include end outs, dirty yarn, holes in the knitted fabric, heavy or light yarn, and a needle run. A secondary consideration for defect detection lies in the manner in which the material is knitted. Standard knitting machines feed the thread into the top of the circular knitting head producing a "tubular" knitted product which depends below the knitting head. This tubular knit rotates as the stitches are produced requiring the optical system to take this movement into account.

In an end out defect, a yarn is missing from the knitted material causing a spiral defect which is usually initiated by broken yarn and which must be detected on the single revolution pass of the tubular knit. The detection system must also have the ability to analyze the manufactured material and determine when dirty yarn, causing discoloration, has been used in the manufacturing process in order to alert the operator of the knitting machine. Holes in the knitted fabric may occur from machine defects or tearing of the knitted material leaving an actual opening in the tubular knit. Heavy or light yarn defects occur when the wrong gauge yarn is utilized in one of the feeding stations and which may be apparent during a single revolution of the tubular knitted fabric. These types of defects may also occur when the yarn becomes crossed and two yarns are found at one particular spot in the knitted material. Finally, a needle run occurs when a needle on the needle cylinder is broken causing a vertical line in the tubular knit fabric and is particularly hard to detect because the occurrence at the inspection station may be masked by the cotton content of the material. Other defects may be difficult to detect due to the fact that they only may be available for inspection at a single instance of a revolution at the inspection station.

Scanners which are presently available for use on jersey or fine material inspect the knit by applying a singular line of light in combination with a photo detector in order to obtain a higher resolution. These systems do not provide a high enough resolution to sort out runs or other anomalies, particularly in fleece material. This is a particularly sensitive issue when attempting to inspect fabric with prior art devices because of their use of a limited number of analog signals. This is additionally complicated in non-continuous defects which may only be viewed on a single revolution of the tubular knit fabric.

Continuous defects such as end outs, heavy or light yarn, or needle runs may be detected but are complicated somewhat by the varying types of fabric manufactured in these machines. The harder to detect faults in the fabric may be classified as spot faults in that they occur transversely as compared to the length way direction of the tubular fabric as it is knitted. Alternatively, the easier to detect continuous faults extend longitudinally along the tubular fabric. While all faults detected will not necessarily require stopping the high speed circular knitting machine, it may still be desirable to record the faults as they occur over a unit of time.

There are a variety of textile monitoring devices for tubular knitted fabric produced on a circular knitting machine. These devices utilize light sources and light detectors, usually photo cells, which are arranged in linear rows and which respond to variations in the reflectance of the fabric. Once the analysis reaches a pre-defined tolerance, the machine is turned off or a default detection signal is indicted. These systems typically utilize electro-optical sensors comprising infrared diodes and photo transistors arranged in alternate rows. However, as mentioned, these known devices fail to discriminate between types of defects or fail to have application on various types of product. U.S. Pat. No. 5,283,623 teaches a method and system for detection of faults in a length of textile fabric wherein six light sources are focused by a condenser onto the knitted structure of the length of fabric. Light reflected than passes back through a transparent disc to photo transistors matching the number of light emitting sources. The analysis method however requires scanning of zones on the fabric strip a number of times before a determination may be made as to defect or fault in the manufacturing process.

None of the prior art devices provide a means for defect detection and analysis for variable type knitting products or which accurately predict the type of defect occurring. Further, none of the prior art references utilize a large number of light emitting and detecting sources in order to increase the accuracy of the determination of fault with the material.

SUMMARY OF THE INVENTION

One object of the present invention is to provide a defect detection system wherein a plurality of construction styled knitting material may be analyzed for defects. A further object of the present invention is to accurately determine the types of defects seen in the knitted fabric. A further object of the present invention is to utilize a wide array of light emission and detection within a compact scanning area in order to increase the inspection capabilities of the detection system.

It is another object of the present invention to provide a digital signal processor which analyzes light reflectance from knitted material which has a learn cycle thereby dynamically changing the threshold values for determination of characteristic defects.

It is an even further object of the present invention to combine both fiber optics and digital signal processing in order to further increase the accuracy of defect detection.

Finally, the present invention comprises a defect scanning apparatus for detection of defects in tubular knitted fabric produced on a circular knitting machine, comprising: a circular knitting machine creating a web of tubular knit fabric; a fiber optic scanning head attached to said circular knitting machine and reflecting light off of said tubular knit fabric and reading said reflected light; a digital signal processor operably connected to said circular knitting machine and said fiber optic scanning head for reading said reflected light signals from said fiber optic scanning head; said fiber optic scanning head further comprised of a light emitting source, an opto-sensor, a first fiber optic bundle carrying light from said light emitting source to said fabric, a second fiber optic bundle reading said reflected light from said fabric to said opto-sensor, wherein said first fiber optic bundle is randomized between said light source and said fabric.

BRIEF DESCRIPTION OF THE DRAWINGS

A better understanding of the invention will be had upon reference to the following description in conjunction with the accompanying drawings in which like numerals refer to like parts and wherein.

DETAILED DESCRIPTION OF THE PREFERRED EMBODIMENT

Figure 1:
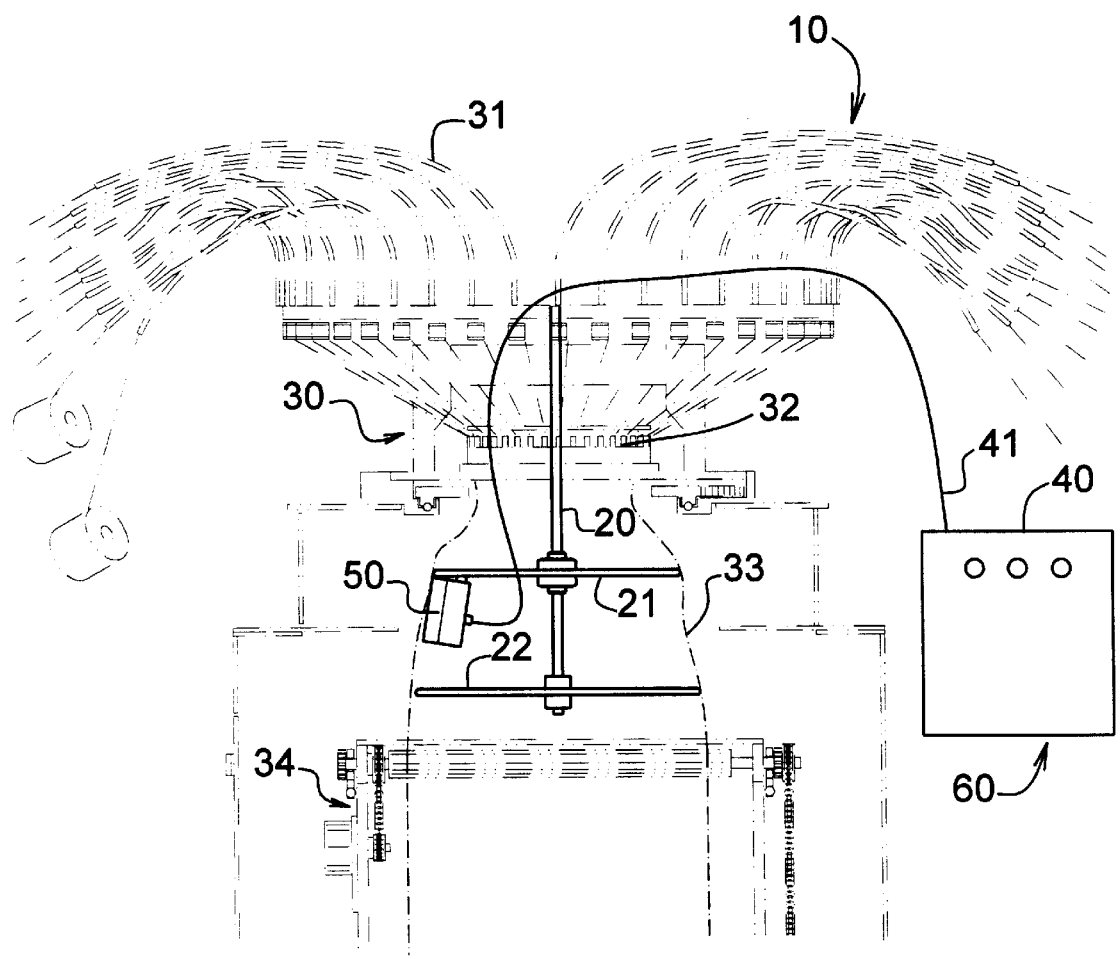
FIG. 1 is a schematic side view of a circular knitting machine with the digital signal processor and scanning head clearly shown.

Shown in FIG. 1 is a circular knitting machine 10 producing a knitted tubular web of fabric 33 which depends below knitting head 30. A plurality of needles 32 on knitting head 30 receive yarn 31 to knit tubular fabric 33 which is pulled through knitting head 30 and wound up in take up apparatus 34. Tubular knit fabric web 33 revolves with support frame member 20 which provides a central axis of rotation for take up apparatus 34. Tubular fabric 33 is expanded around circular frame members 21 and 22 prior to storing in a large fabric roll located in take up assembly 34. Take up assembly 34 additionally rotates with support frame member 20 and is driven by a separate drive motor not shown. Circular frame member 21 does not rotate under knitting head 30. Knitting head 30 knits tubular fabric until the roll in take-up assembly 34 is a desired weight.

Rotating tubular knit material 33, after formation by needles 32 and knitting head 30 is continuously scanned by optical scanning head 50. Optical scanning head 50 is of sufficient vertical length that enough of the tubular fabric 33 is scanned upon each revolution of the fabric web such that after a single revolution of web 33 head 50 is directly above the previous scan path. Optical scanning head 50 effectively covers 100% of the newly knitted tubular fabric as it is knitted and rolled into take up assembly 34.

Figure 10:
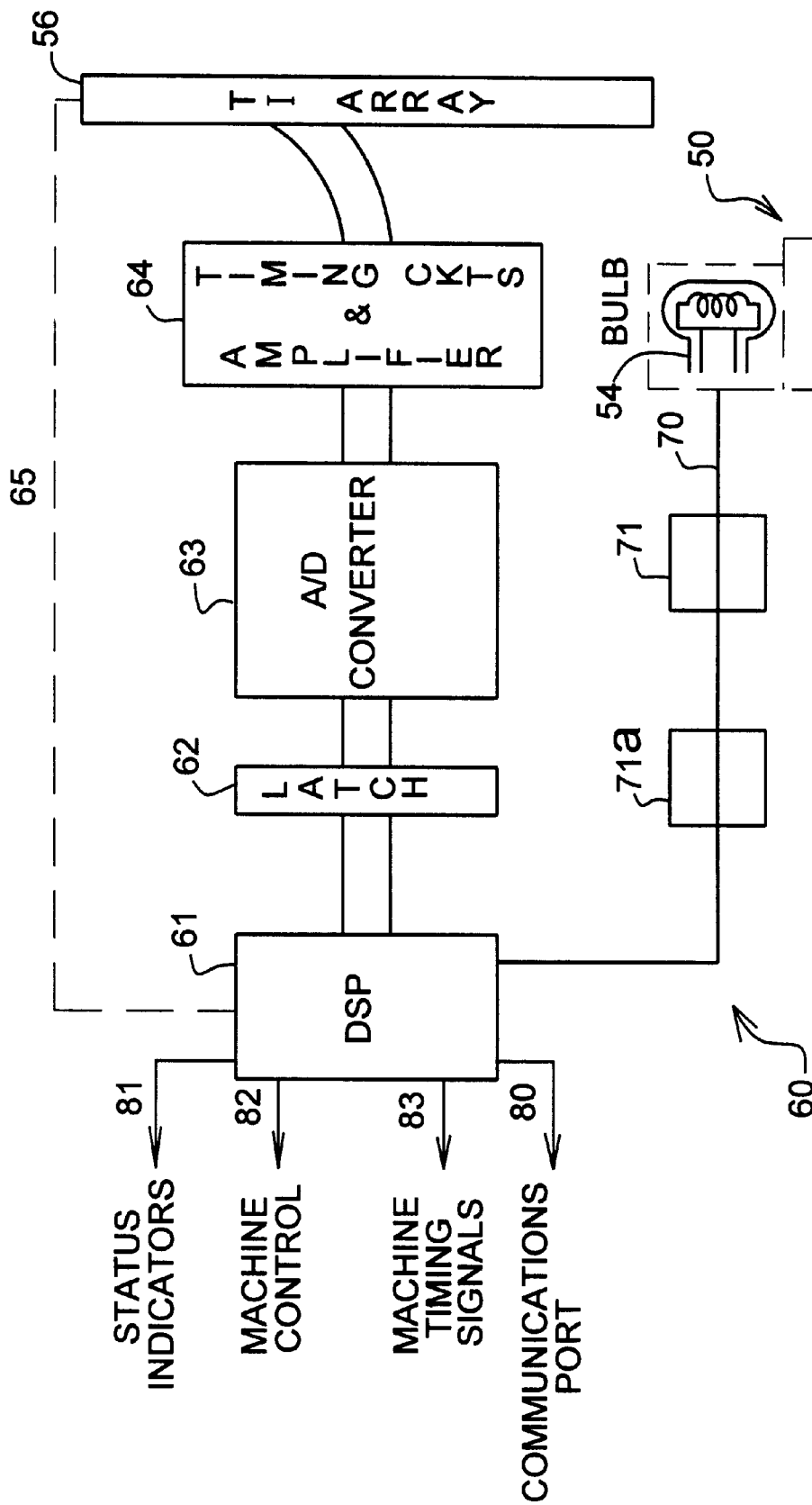
FIG. 10 is a schematic of the digital signal processor circuit of present invention.
Figure 11:
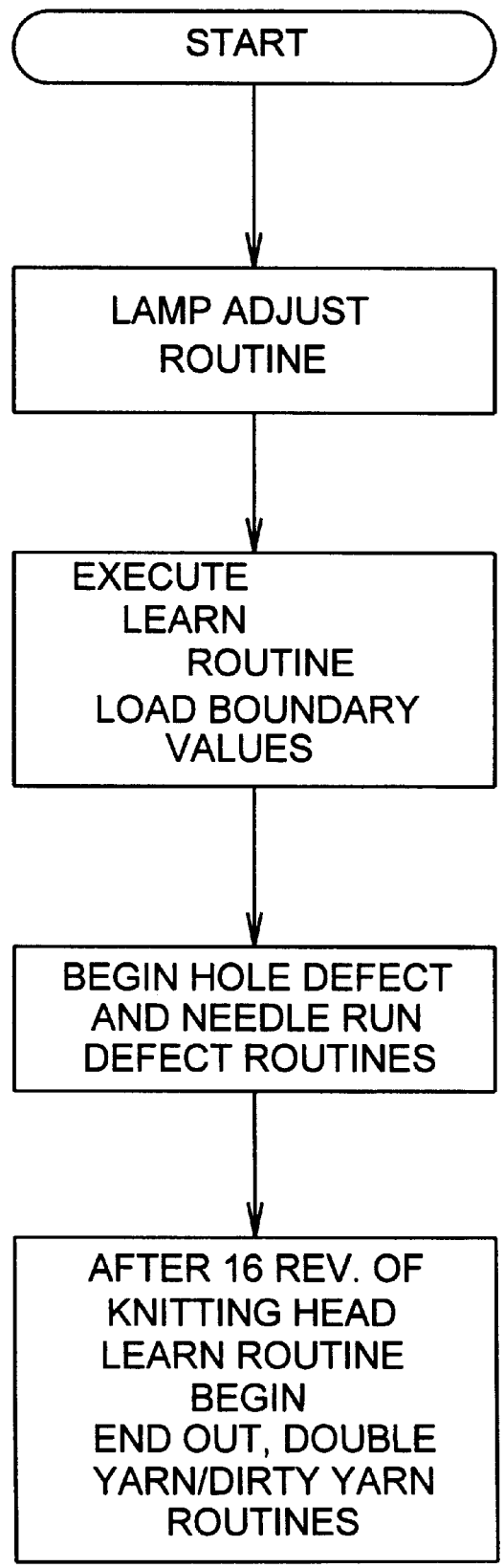
FIG. 11 is a flow chart of the overall machine software control routine of the present invention.

The present invention analyzes fabric web 33 through the use of a digital signal processing system 60. The digital signal processing system 60 of the present invention is generally comprised of optical scanning head 50, interconnecting cable 41 and housing 40 which holds a digital signal processor and other electronic components to be discussed herein. The electronic component housing 40 contains the digital signal processing system components which work in conjunction with the scanning head 50 and which is operably connected to knitting machine 10 for control thereof. The system components of digital system 60 include, as shown in FIG. 10, a digital signal processor 61, an intelligent opto-sensor or pixel linear array 56, amplifier and timing circuits 64, analog to digital converter 63 and a data latches 62. Additionally, a light source such as a bulb 54 must be utilized to direct light onto the interior surface of fabric web 33. The light source 54 is controlled by a regulator 71 which in turn is controlled by a digital potentiometer 71a. This lighting electronics comprised of the bulb 54, regulator 71 and potentiometer 71a is in turn controlled by the digital signal processor 61.

In general, the digital signal processor system 60 of the present invention analyzes successive strips of the web of material 33 manufactured by needles 32 of knitting head 30. As previously described, knitting head 30 knits the tubular web of material 33 which then drops below the knitting head 30 into take up assembly 34. Placed directly against or adjacent to the interior of the tubular knitted web 33 is found scanning head 50. Scanning head 50 is shown in close up in FIG. 5. Associated with the scanning head 50 is a light source 54 which is held into place by bulb retaining means 51. Light source 54 is an incandescent lensed bulb with a fairly sturdy filament. Light from bulb 54 is carried through scanning head 50 via a plurality of fiber optic lines 57a, as is shown schematically in FIG. 7, which carries the light to the end of the fiber optic lines 57a. Reflected light is then received within the scanning head 50 through the end of fiber optic lines 57b and carried to a pixel linear array 56. This reflected light sensed by the pixel array 56 is then transformed and analyzed by a digital signal processor 61 which determines, based on the reflected light obtained via fiber optic lines 57b, whether or not defects have been sensed in tubular knit web 33.

As previously noted, scanning head 50 inspects the entirety of tubular knit web 33 as it rotates about circular knitting frame members 21 and 22 while at the same time moving in the downward direction into take up assembly 34. Digital signal processor system 60 further utilizes software algorithms to make determinations as to the existence of the five defects listed herein, namely: end outs; needle run; dirty yarn; heavy or light yarn; and hole defects. Digital signal processor system 60 is also operably connected to the circular knitting machine 10 in order to stop the machine from knitting once a defect has been detected and to signal the operator of knitting machine 10.

Figure 2:
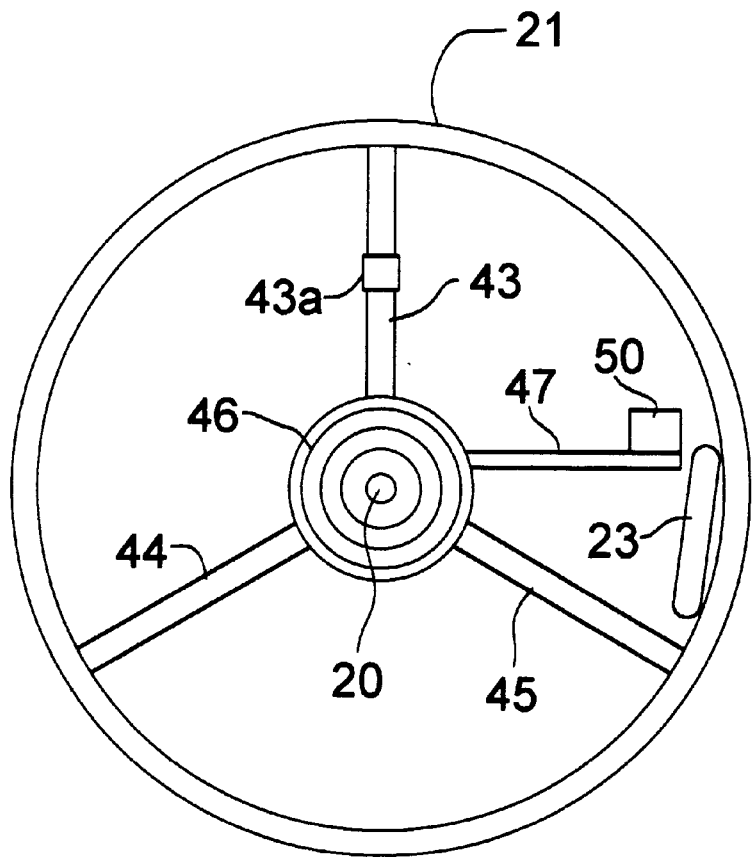
FIG. 2 is a top view of the circular knitting machine frame and scanning head attachment.

Knitting machine 10 has circular support frame members 21 and 22 depending below knitting head 30 and held in place by rotating vertical support member 20. Upper circular frame member 21 has a smaller diameter as compared to lower frame member 22. As shown in FIG. 2, vertical support frame member 20 holds circular frame member 21 via spoke members 43, 44 and 45. Lower circular frame member 22 is of similar construction but rotates with member 20. Unlike lower frame member 22, upper frame member 21 does not rotate with vertical support member 20 but remains stationary. Hub 46 has bearings which allow the member 20 to freely spin within. Bracket 43a extends upwardly from spoke member 43 to hold the upper circular frame member stationary while member 20 rotates. Bracket 43a is securely attached to an interior portion of the frame of the knitting machine.

Figure 3:
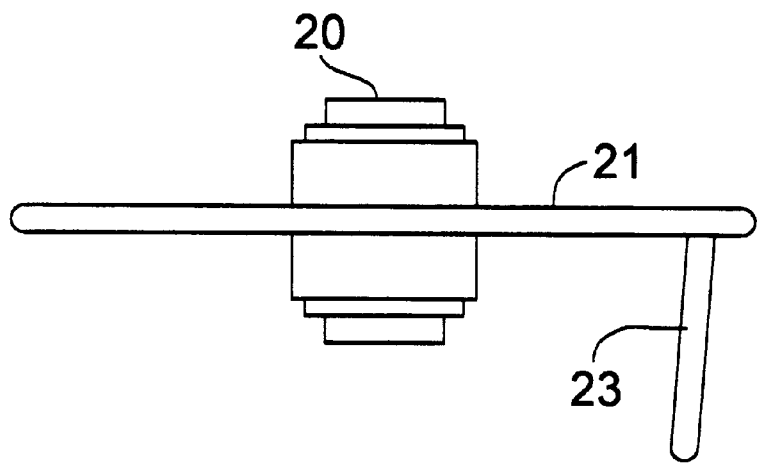
FIG. 3 is a side view of the circular knitting machine frame and side bar attachment.
Figure 4:
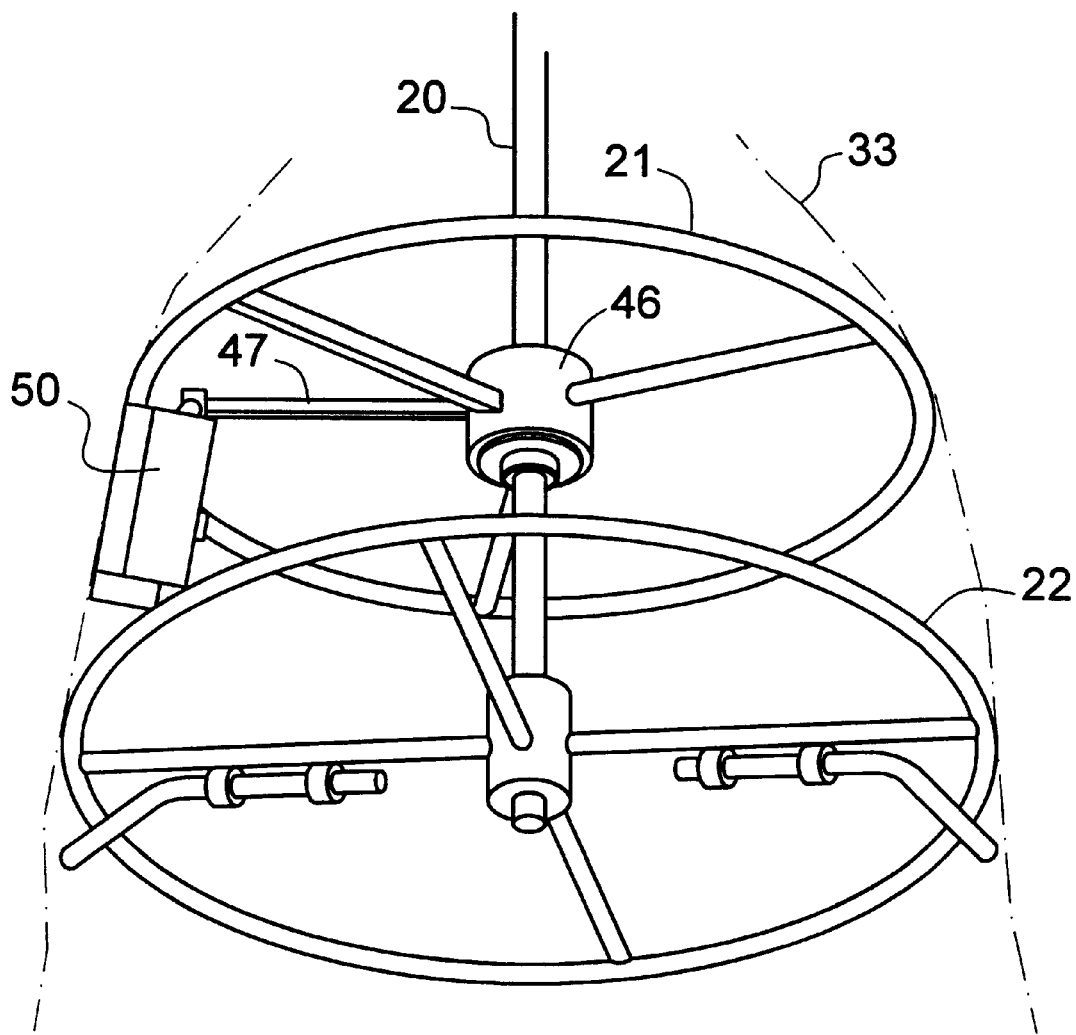
FIG. 4 is a close up view of the circular knitting machine frame and method of attaching the scanning head to the knitting machine.

Scanning head 50 is attached to attachment arm 47 which is shown in FIGS. 2 and 4. Attachment arm 47 is fixedly attached to hub 46 in order to extend digital scanning head 50 at the periphery of circular support frame 21 and immediately adjacent to tubular web 33. Mounted below and attached to upper circular frame member 21 is defraying bar 23 which prevents the rotating tubular web 33 containing defective large holes from snagging or tearing on scanning head 50. As is shown in FIG. 3, defraying bar 23 has a slight inwardly inclined angle. Scanning head 50 is not shown herein to more clearly display bar 23. While defraying bar 23 prevents the tubular web 33 with large holes from snagging scanning head 50, it is desirable to keep the fiber optic lines 57b and area 52 of scanning head 50 directly flushed against tubular fabric web 33 so that proper readings may be made by the scanning head and the reflectance of the material may be correctly measured.

Figure 5:
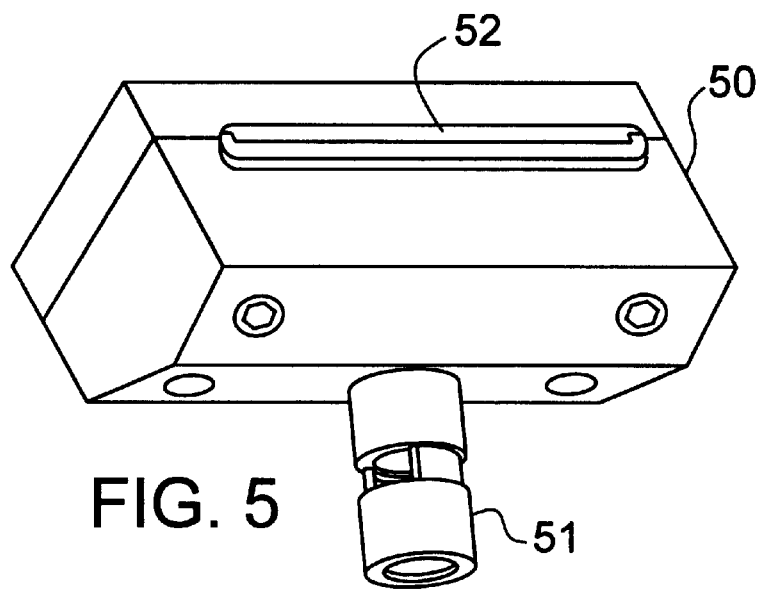
FIG. 5 is a perspective view of the scanning head of the digital signal processing system of the present invention.
Figure 6:
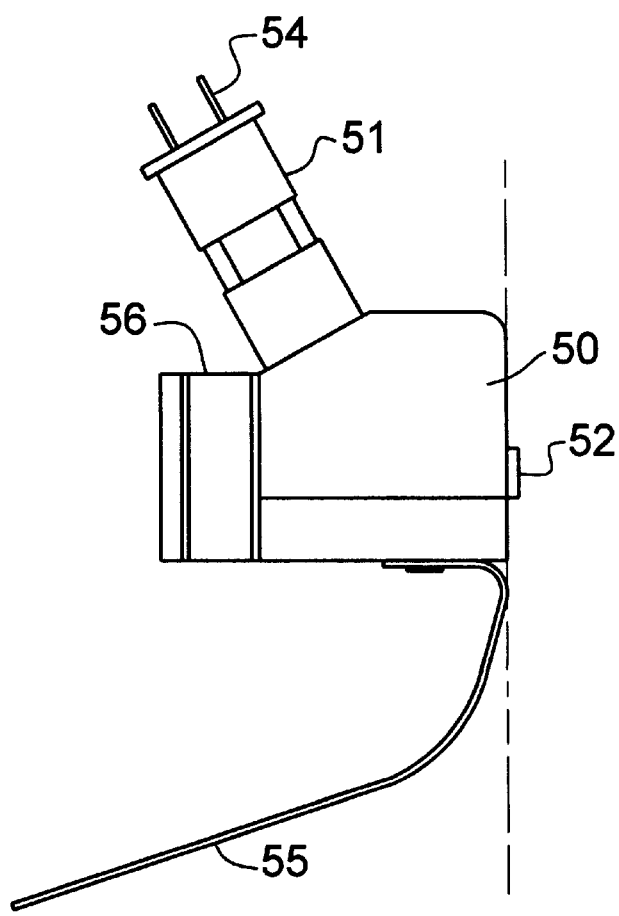
FIG. 6 is a top view of the scanning head and shielding arm of the system of the present invention.
Figure 7:
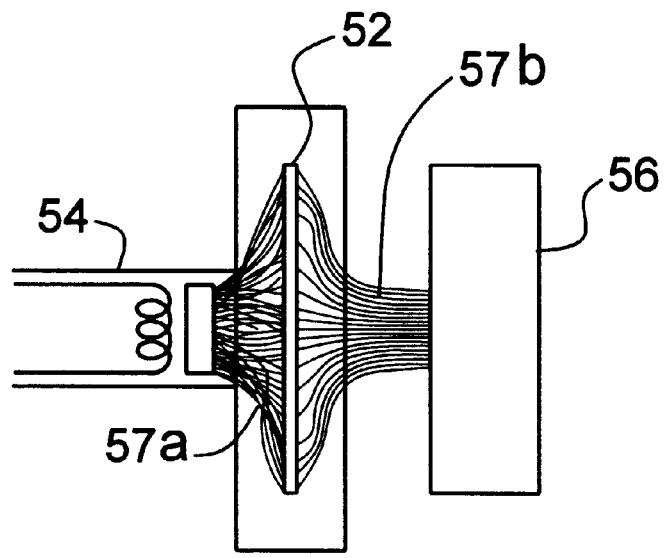
FIG. 7 is a schematic view of the internal connections between the light emission source and the scanning head of the present invention.
Figure 8:
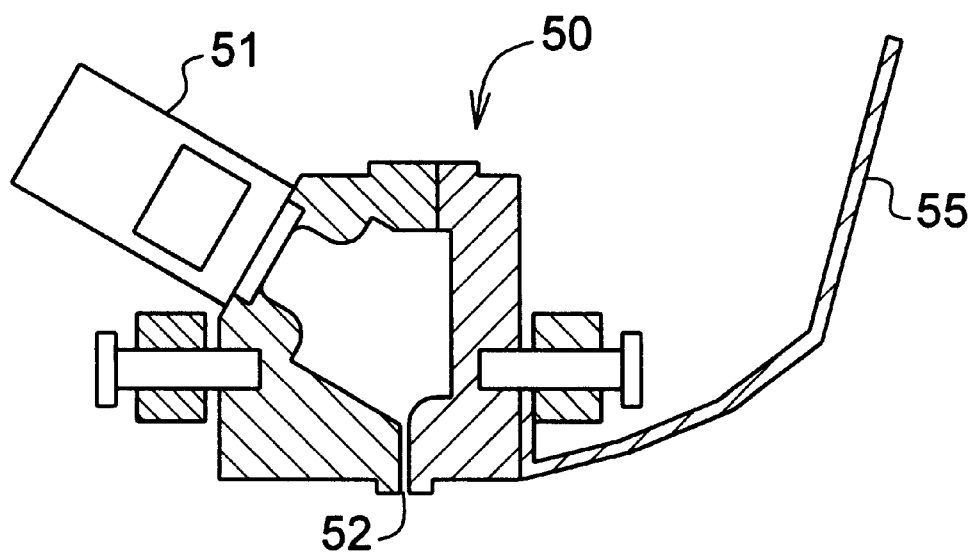
FIG. 8 is a top cut-a-way view of the scanning head of the present invention.
Figure 9:
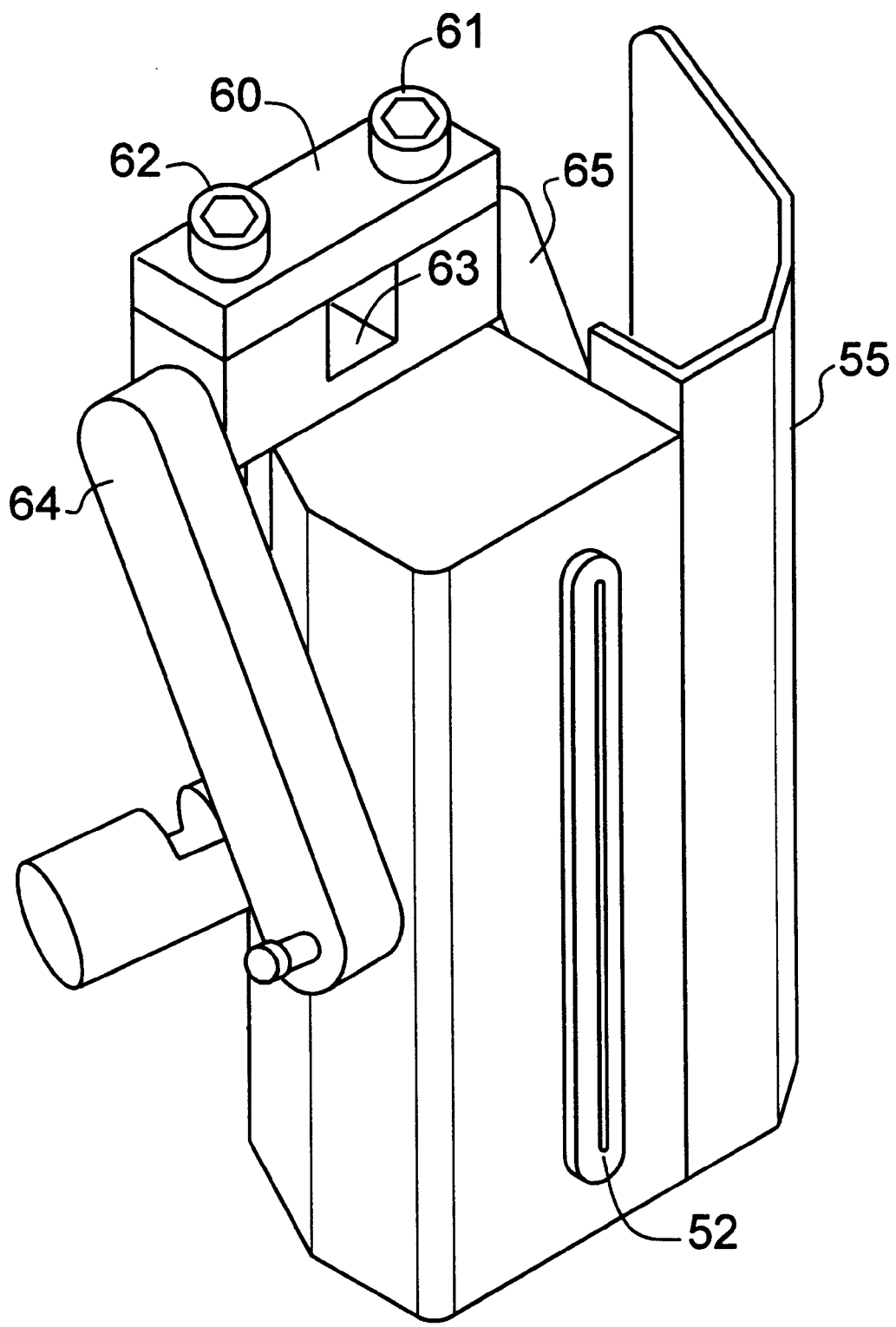
FIG. 9 is a perspective view of the scanning head and attachment brackets utilized in the present intention.

Shown in FIG. 5 is the fiber optic scanning head 50 of the present invention. Light bulb receptacle or retaining means 51 and fiber optic line 52 are clearly shown. Fiber optic line 52, after attachment of the scanning head 50 to attachment arm 47, compresses directly against the interior of tubular knit material 33. Bulb receptacle 51 retains incandescent bulb 54 therein, said bulb being a lensed bulb directing light towards the interior of scanning head 50. Lensed bulb 54, shown in FIG. 6 and FIG. 7, is controlled by the digital signal processor 61 via a voltage regulator 71 and digital potentiometer 71 a shown schematically in FIG. 10. Digital signal processor 61 controls the voltage to bulb 54 in order to vary the brightness of the bulb dependant upon the current style of material scanned by scanning head 50. Returning to FIG. 7 scanning head 50 has interiorly held therein a fiber optic bundle 57a and 57b and a pixel linear array 56, both of which transmit and read data from fiber optic line 52. Fiber optic scanning head 50 evenly disburses light given off of bulb 54 by randomizing fiber optic bundle 57a to fiber optic line 52. Randomizing the fiber optic bundle 57a from the bulb 54 to the fiber optic line 52 removes any irregularities in the light emission from the lensed bulb 54 thus spreading the emitted light evenly along fiber optic line 52 and hence material web 33. Light reflected by fabric web 33 and read at scanning lens 52 is transmitted to a pixel linear array 56 by second fiber optic bundle 57b for conversion to digital signals. Fiber optic bundle 57b is not randomized so that the correct orientation and placement of reflected light from web 33 may be determined on pixel linear array 56. This allows digital signal processor 61 to correctly position irregular reflectance values on web 33 based upon specific pixels in pixel linear array 56 reading said value.

The fiber optic material carrying light given off by bulb 54 to the fiber optic line 52 and returning the reflected light to the pixel linear array 56 is a standard quality glass fiber optic light transmitter and is used primarily for the accuracy in carrying light waves but is unaffected by machine oil. The fiber optic bundles 57a and 57b are embedded into the interior of scanning head 50 which therefore removes any interference from exterior sources. Fiber optic scanning head 50 used in the present invention allows specific reflected light data to be retrieved from the material web 33 such that accurate data may be produced. Additionally as seen in FIG. 6, scanning head 50 has cloth defraying bar 55 allowing the fiber optic line 52 to be placed directly against the web 33 and allowing the rotating cloth web 33 to pass thereby without catching on other areas of the scanning head.

Scanning head 50 has the bulb 54 and the pixel linear array 56 included therein for close proximity and reduced fiber optic length. The lensed bulb 54 is a focused lensed bulb such as a 5 volt bulb, part number L8050, produced by Gilway, said bulb 54 controlled by the digital signal processor system 60 of the present invention through a voltage regulator 71 and digital potentiometer 71a as shown schematically in FIG. 10. The control of the bulb 54 through a voltage regulator 71 allows the system to adjust the brightness of the bulb 54 for varying cloth types and allows the system to dynamically adjust the brightness of the bulb during startup so as to utilize the most optimal voltage and thus brightness for high quality reflectance data generation.

Turning to FIG. 10, a schematic diagram of the electronic components controlling the digital signal processor and defect detection system 60 of the present invention is shown. As previously indicated, bulb 54 and scanning array 56 are incorporated in the fiber optic scanning head 50. The fiber optic scanning head 50 is operably attached to the control box 40 which contains the electronic components of the digital signal processor system 60. As shown in FIG. 10, the digital signal processing system 60 of the present invention is comprised of a digital signal microprocessor chip 61 such as an ADSP-2181 manufactured by Analog Devices. The digital signal processor 61 is connected to a latch 62 which itself is connected to an analog to digital converter 63. Converter 63 receives input from an amplifier 64, said amplifier operably connected to the optical scanning array 56 previously mentioned. Reflected light is carried by the fiber optic bundle 57b to scanning array 56 which is a 512 pixel array and which may be CCD or other light sensitive device. Scanning array 56 is an intelligent opto-sensor which measures the reflected light from the fabric web 33. These reflected light signals are translated into 510 voltage measurements by the plurality of pixels in the array 56, each measurement of which is amplified by amplifier 64 prior to conversion to a digital value. Amplifier 64 will increase each measured signal to a value from 0 to 5 volts.

The digital signal processor 61 of the present invention, shown schematically in FIG. 10, is also operably connected to a communications port 80, status indicators 81 which are located on or near knitting machine 10, machine control lines 82 and machine timing signals 83. A communications port 80 is a standard RS-232 serial communications port and provides a means to input data to the system 60 indicating the particular type of material being used, sensitivity values and other operational values necessary for adjustment of machine operation conditions. Status indicators 81, sown schematically, may be lights or other means to communicate error conditions to the operator of knitting machine 10. Various lights may be provided for different error conditions or warnings which the system 60 determines to be existent in the web of material 33 or other problems associated with machine hardware. Machine control line 82 may be connected to the system 60 for control of knitting machine 10. If processor 61 determines an error condition existent in the web of material 33, knitting machine 10 may be stopped in order to prevent additional defective material being knitted. Additionally, in order for the processor 61 to correctly determine certain defects, machine timing signals 83 must also be provided. This allows the processor 61 to determine knitting head positioning, revolutions and other parameters.

Array 56 is a serial output device controlled by a separately generated timing signal. Array data signals are sent by the array 56 in sequential order. The serial output for each successive array pixel in the array 56 is amplified by amplifier 64 and then converted to a digital value by A/D converter 63. There is also a timer circuit, as is shown in FIG. 10, which works to control the flow of data to and from the array 56. The timing circuit 64 has two functions. One is a clock which controls the charge transfer, pixel output and reset of the array. The other function of the timing circuit 64 is to act as a serial input which defines the start of the data out sequence of the array 56.

The analog to digital converter 63 is a high speed 8 bit resolution A/D converter which receives the pixel voltage data sequentially and passes this voltage signal to one of the two data latches 62. Data latches 62 are 8 bit latches allowing for 2 individual pixel data values to be transferred to the digital signal processor 61 at any given data transfer opportunity. Therefore, the first latch of the latch pair 62 receives the first 8 bit pixel voltage value. The digital signal processor waits for the next sequential 8 bit pixel voltage value before beginning a data transfer to the second latch in the latch pair 62. Once the second value is loaded into latch 62 from the converter 63, both values are passed to a 16 bit input register on processor 61 for separation and sequential analysis.

The pixel linear array 56 is a 512×1 linear array. The end pixel values are discarded and not used providing a total of 510 pixels available for inspection. The linear array 56 is an intelligent opto-sensor such as Texas Instruments TSL218 pixel linear array or other suitable device. The array has a 512 bit shift register which controls the transfer of the array data from the pixels to the amplifier and the analog to digital converter. A single pixel value is provided from the array 56 to the output every two micro-seconds. Therefore, the entire 512 pixel array cycles in 1.024 milliseconds. A clock or timing circuit which is not shown in FIG. 10 controls the timing sequence of the array 56, latch 62 and microprocessor 61 in combination. The serial output of array 56 is controlled by said clock which runs at up to 500 kHz. The timing circuit is timed with latches 62 and processor 61 to send interrupt signals for the data latches 62 and control thereof. Additionally, array 56 has an end of array interrupt signal 65 in order to indicate the last data value in the array has been transferred to processor 61. This allows the circuit elements to re-synchronize at each end of array interrupt.

Processor 61 is operably connected to bulb 54 via voltage line 70 which has interconnected therein a voltage regulator 71 and digital potentiometer 71 a for proper control of the light emission emanating from bulb 54. Processor 61 controls the brightness of bulb 54 and during the preliminary learning and adjustment stages of the defect detection system and adjusts the voltage of bulb 54 to an optimal reflectance for detection by array 56. Therefore, known minimum reflectance values are utilized to adjust the voltage to bulb 54 for a given fabric type. Minimum and maximum pixel voltages are loaded into processor 61 based upon the type of materials and for each pixel in array 56. These upper and lower boundaries are utilized to adjust the voltage of bulb 54 so that accurate data is provided to the system for analysis.

As previously mentioned, processor 61 is a digital signal processor microcomputer optimized for high speed digital signal processing. Processor 61 has a 16 bit serial input port for receiving data submitted by the two latches 62. As indicated however, a separate clocking circuit controls the timing of the processor 61, latch 62, array 56 and other circuitry. This clock circuit provides interrupts to the processor 61 and a clock signal for the array 56 in order to control and synchronize data transmission. This clock circuit also provides hand shaking capabilities between the analogue to digital converter 63, array 56, latches, and digital signal processor. This independent and high speed clocking circuit is needed to control the high data transmission exchange rates coming from the array 56 and going to the processor 61. Serial output from the pixel array 56 is provided to the processor 61 two pixels values at a time such that all 510 pixel values are read by processors 61 in 1.020 ms.

Control software is provided to the digital signal processor 61 by an on-board EPROM which is contained within housing 40. This control software allows the processor 61 to analyze the array signals sequentially two at a time as they enter into the processor 61 in order to determine the existence of the five defects previously mentioned. For other defect detection purposes, the processor 61 also keeps a running tally of the average or sums of the pixel value voltages which enter into the processor. Individual software routines are provided to determine the existence of each of the five fabric defects. Upon entry of operator input as to the type of fabric being knitted by circular knitting machine 10, processor 61 loads default threshold values for array pixels in a data array. These default values may be dynamically adjusted during a learning cycle the system goes through upon initial startup of the knitting machine 10. This dynamic adjustment of threshold values during a learning cycle allows the digital signal processing system 60 of the present invention to adjust threshold values for anomalies caused by bulb 54 characteristics, reflection variabilities, differing types of material webs 33, systems performance and other variables.

The learning cycle which the system initiates upon startup of knitting machine 10 is a two stage process the first stage of which consists of four revolutions of the tubular knitted fabric in order to develop and adjust the threshold values for upper and lower boundaries. These upper and lower boundaries allow the digital signal processor system 60 to determine the existence of specific defects by comparing the array pixel data to boundary values. These lower and upper threshold boundary values may need to be crossed by a given number of sequential pixels on a single knitting head revolution in order to indicate the existence of a defect or the boundary crossings may require continued observation for a particular number of revolutions for defects to be detected and signaled.

The first stage of the learning cycle is comprised of four revolutions for adjustment of the upper and lower threshold values to dynamically change predetermined thresholds stored in system flash memory. For heavy or light yarn defects and for end out defects, the system 60 of the present invention can determine the existence of the defect on a per revolution basis. For defect detection of a hole in the cloth web, dirty cloth or for needle run defects, the system of the present invention utilizes averages for comparison of optically sensed values in order to determine the existence of the defect. More particularity for each section of software and the specific methodology for determining defects and table averaging will be provided herein.

Figure 12:
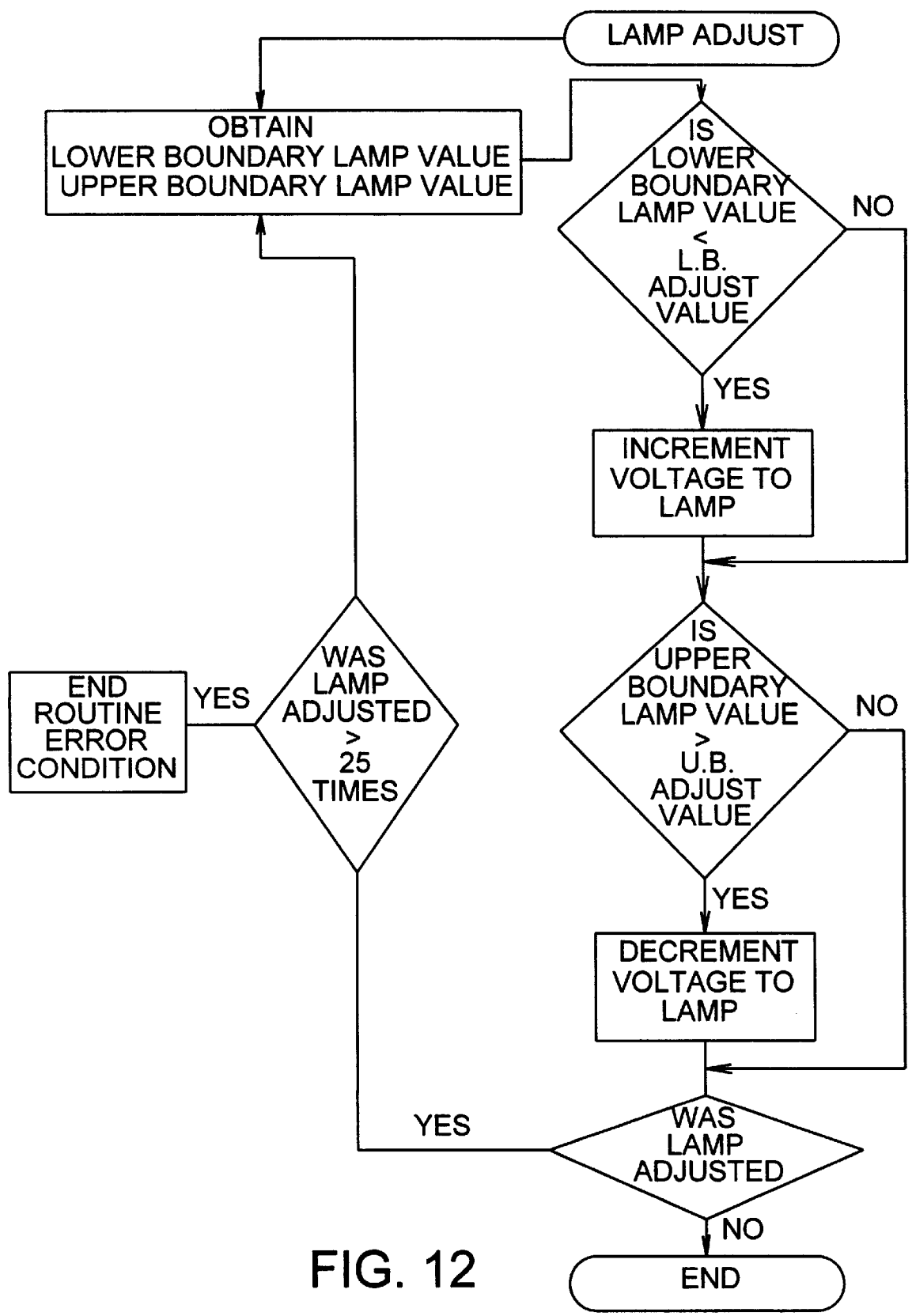
FIG. 12 is a flow chart of the lamp adjust software routine of the present invention.

During initialization of the digital signal processor system 60, a lamp brightness adjustment routine is initiated so that the bulb 54 is at optimal voltage and brightness increasing the reflectance of light off of the web of material 33. A flow chart of this lamp adjust routine is shown in FIG. 12. Bulb 54 is controlled by voltage regulator 71 and a digitally controlled potentiometer 71a through control line 70, shown in FIG. 10. Digital signal processor 61 executes this lamp adjust routine, represented in FIG. 12, in order to set the bulb to the correct voltage. Typically, this voltage value is between 2.1 and 2.3 volts. During this initialization routine, since the individual pixel voltages generated by array 56 are not uniform, each pixel has an individual upper and lower voltage boundary stored and analyzed by system 60. Default upper and lower boundary array voltages are developed from testing and adjustment of the bulb 54 and stored in EPROMS. The upper boundary array value for each pixel is the maximum voltage value observed for a given pixel during a startup routine. A lower boundary array value is a value for each pixel comprising the minimum voltage value observed during a startup routine. Sums of the arrays are calculated and stored in the variables upper boundary lamp value and lower boundary lamp value. There are additionally utilized empirical values, downloaded from a palm top computer or other system by the operator of the machine 10. The lower boundary adjust value represents the lower magnitude limit for the lighting, based on the style of material being knitted. A similar empirical value is obtained for the upper boundary adjust value. The effective goal of this bulb or lamp initialization routine is to get the lamp or bulb 54 to an optimized brightness value by reading each pixel value and comparing it to known empirical upper and lower voltage values.

After the digital signal processor 61 has calculated the upper boundary array and lower boundary array representing the maximum and minimum voltage values observed during a predetermined number of revolutions, the lamp adjust routine begins in order to adjust the lamp or bulb 54 to the proper optimal voltage. As previously stated, the upper boundary lamp value is calculated as the upper sum of the upper boundary array. The lower boundary lamp value is calculated as the sum of the lower boundary array. The empirical values down loaded from the operator's palm top computer or other means for the specific type of material being knitted are stored in two variables, the lower boundary adjust value and the upper boundary adjust value. The digital signal processor 61 compares the lower boundary lamp value to the lower boundary adjust value. If the lower boundary lamp value is less, then the digital processor 61 increments the voltage to the bulb 54 to a higher voltage value via the digital potentiometer 71a and the voltage regulator 71. Next, the digital signal processor 61 compares the upper boundary lamp value to the upper boundary adjust value. The upper boundary adjust value, as indicated, provides the upper magnitude limit for the lighting. The digital signal processor 61 decrements the lamp voltage to a lower value via the digital potentiometer 71a and voltage regulator 71 if it finds the upper boundary lamp value larger than the upper boundary adjust value. The lamp adjust routine is terminated when the digital signal processor 61 does not need to further adjust the lamp voltage. If a voltage adjustment is required, the software re-runs the lamp adjust routine loop. If after 25 consecutive loops the digital signal processor could not properly adjust the voltage, the system 60 stops the knitting machine 10 and indicates a defective component condition.

After adjustment of the bulb voltage value to an appropriate level, the upper and lower boundary arrays are relearned. Just as in the lamp adjustment routine, these defect routines are dynamically adjusted in order to optimize performance of the system 60 by changing boundary conditions during a learning stage. There are two boundary array values which are learned during a five revolution learning period of the knitting machine 10. These are the boundary values which determine the existence of a needle run and a hole defect. The hole defect routine uses the lower boundary array which is developed during the learning stage. Alternately, needle run errors are determined using the lower boundary array and the minimum average voltage per scan calculated during the learning stage.

Figure 13:
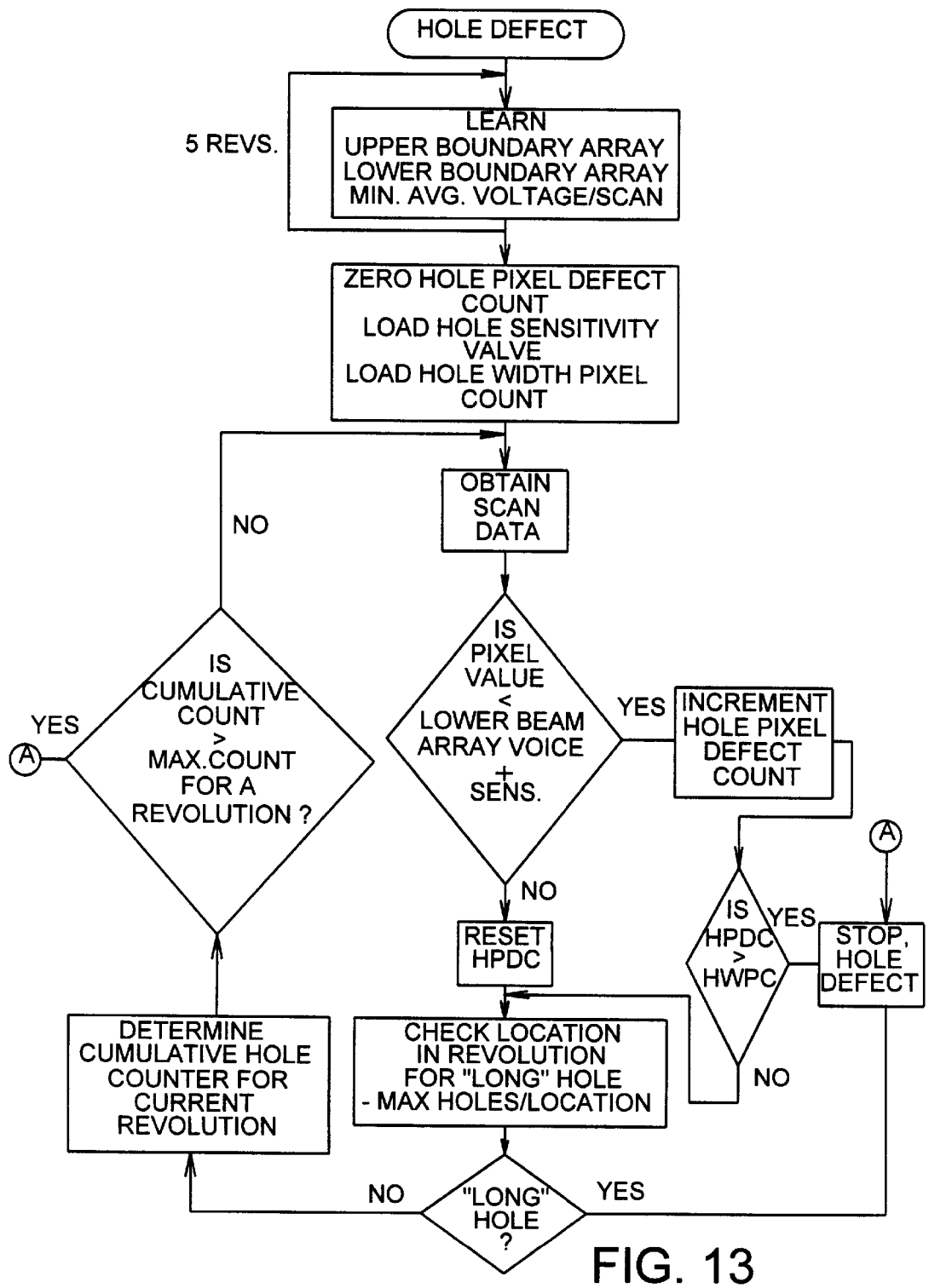
FIG. 13 is a flow chart of the hole defect software routine of the present invention; and, FIG. 14 is a flow chart of the needle run software routine of the present invention.

After the five revolutions of the knitting machine 10 during the learning stage, the digital signal processor system 60 begins looking for hole defects in web 33. Hole defects are determined by the hole defect routine represented in the flow chart of FIG. 13. Hole defects in the web of material 33 cause the reflected pixel voltage values read from the array 56 to have a voltage below recorded values in the lower boundary array. Loaded from a palm top or other computer controlled by the operator of the knitting machine 10 is a hole sensitivity value and a hole pixel count value. The hole sensitivity value is an empirical value predetermined to insure that false positive indications of holes do not occur. The hole pixel count value is a predetermined value of the necessary width of a hole to be found in the web 33 before a hole defect is signaled to the operator. During operation of the system 60 for determination of a hole defect, each pixel from the array 56 is analyzed and compared to the corresponding value and the lower boundary array. If the pixel voltage value is less than the corresponding lower boundary array value plus the hole sensitivity value downloaded by the operator, a hole is indicated and the hole pixel defect count is incremented. Otherwise, the system 60 continues analyzing the next available pixel voltage value. If the hole pixel defect count is incremented then it is compared with the downloaded hole pixel count to determine if the width of the hole is greater than the downloaded hole width error value. If the hole in the web of material 33 is large enough (i.e. the count is larger then the downloaded width count), a hole is indicated the knitting machine is stopped. If the hole is not wide enough, then the digital signal processor 60 compares the hole count at a given linear location in the revolution to a downloaded value representing the maximum consecutive or lengthwise vertical hole count for any given location in the revolution. This effectively allows the digital signal processor to analyze the vertical length of holes in web 33 which may occur in a multiple number of sequential revolutions. If this were not done, holes which were not wide enough to cause the system to shut down may occur over multiple revolutions causing extended lengthwise holes. If the hole count for the particular location in the revolution is greater than the maximum holes allowed per location, the machine is stopped and an error is indicated. Otherwise, a final hole comparison is conducted to determine if the number of holes signaled per revolution of the knitting head 30 is greater than a predetermined number. If this maximum hole indication per revolution is greater than a predetermined number, then the machine is stopped. Otherwise defect analysis continues.

Figure 14:
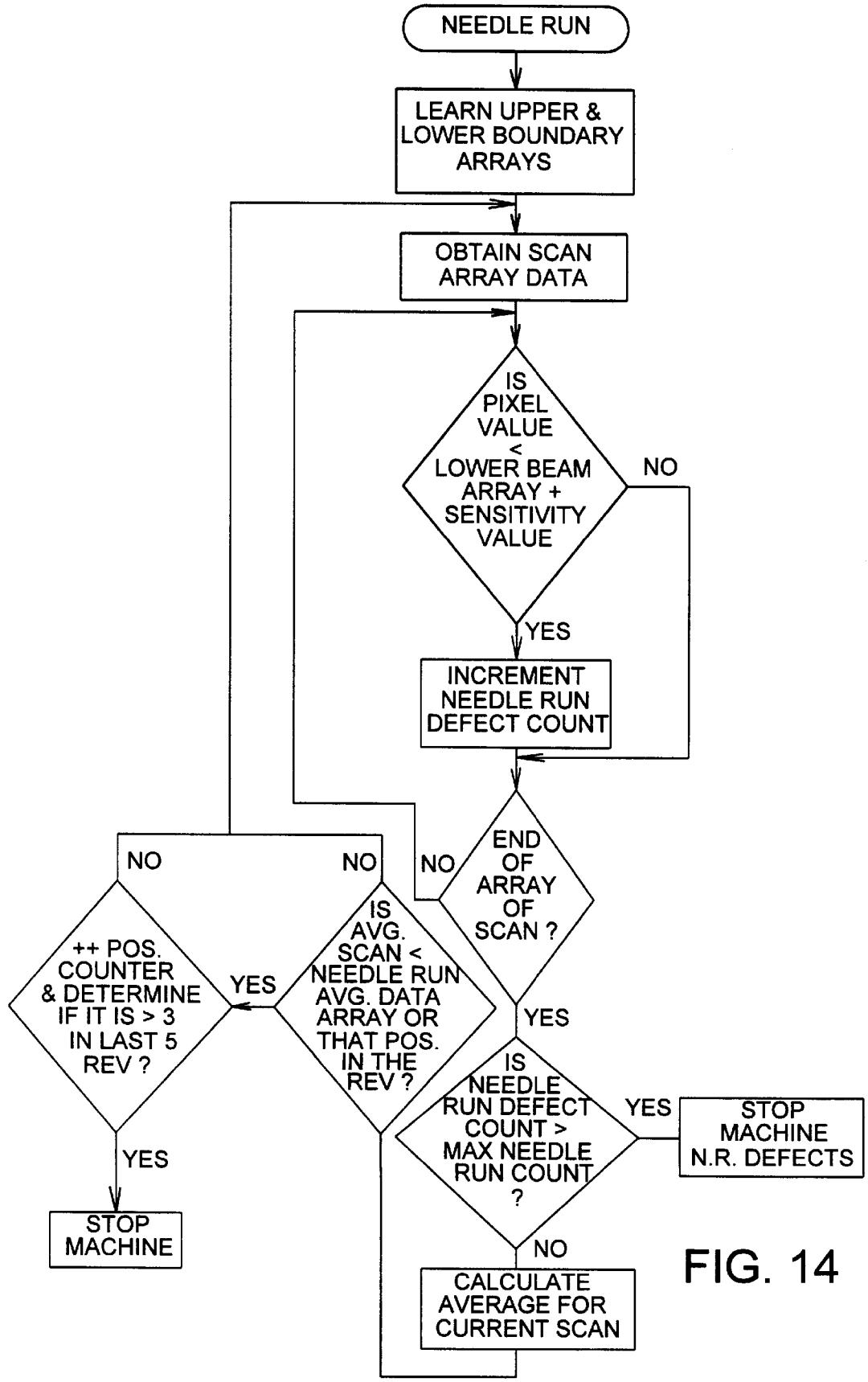

The digital signal processor system 60 scans for holes and needle run defects in the web of material 33 at the same time. The digital signal processor system 60 detects needle run defects in the web of material 33 by two different methods, represented in the flow chart shown in FIG. 14. Since needle run defects occur in vertical form and are not found in a particular single revolution, values must be stored for defects found and the location of the defect in the given revolution. The first detection method utilizes the lower boundary data array value previously calculated. The digital signal processor 61 compares the individual pixel voltage value to the corresponding lower boundary array value adjusted by a sensitivity value which is downloaded from a palm top or other source operated by the machine operator. If the current pixel voltage value is less than the lower boundary array value plus this downloaded sensitivity value, a needle run pixel defect count is incremented. At the end of a pixel array 56 scan, the digital signal processor 61 compares the needle run pixel defect count to the maximum needle run pixel defect count which is additionally downloaded from a palm top or other source entered by the operator of the machine. If the digital signal processor 61 finds a needle run pixel defect count larger than the maximum needle run pixel defect count, it stops the knitting machine 10. The second method for determination of a needle run defect in the web 33 of material is through the use of average pixel values for a complete scan of the pixel array 56. The digital signal processor 61 calculates an average scan voltage value for the current complete scan of the pixel array. The processor 61 then compares the average value for the current scan to the needle run average data array value which was previously determined. This array value is the average scan value determined for an entire revolution of the circular knitting machine during a learning stage. Since there will be a plurality of scans in any given revolution of the knitting machine 10, there are a plurality of average values in this data array corresponding to given segment locations in the revolution of the knitting head. The processor then compares the average value for the current scan to the needle run average data array value which corresponds to the knitting machine segment revolution position for the web of material 33. If the average value for the current scan is less than the needle run average data array value plus a needle run average sensitivity value downloaded from a palm top or other source operated by the operator, a counter is incremented for the physical position of the knitting head where the defect is detected. If the counter is incremented for a particular position in the revolution more than three times in five revolutions of the knitting machine 10, the digital signal processor system 60 stops the knitting machine 10 and indicates that the web of material has a needle run defect condition.

For light yarn, heavy yarn, end out and dirty yarn conditions, only two other boundary values are needed. An end out lower boundary value is utilized to determine both light yarn and end out conditions. Further, a double yarn upper boundary value is utilized to determine the existence of heavy yarn and dirty yarn conditions. For the end out lower boundary value, a learning routine is run during the first 16 revolutions of the knitting head 30. The low boundary voltage is compared to pixel data read from array 56. For each revolution during the learning mode, a summation count is determined for the number of pixels lower than the low boundary voltage value. Each of these 16 low boundary summations is stored in a stack. A sum is kept of the entire stack of low boundary crossings per revolution. This calculated sum is now the learned value for determination of an end out condition. During actual operation of the system 60 for determination of an end out condition or light yarn condition, this sixteen revolution stack of the sum of pixel voltages below the lower boundary voltage is utilized. Comparison of this rolling sum to the learned sum of the stack provides indication of light yarn or end out conditions. After each revolution of knitting head 30, the sum value calculated is pushed onto the stack and the oldest value is removed. The rolling sum value of the stack is then adjusted for this stack push operation. In addition, a tolerance or sensitivity offset value is utilized to adjust the learned sum value during comparison to the rolling stack sum in order to remove noise from the system, just as in the needle run and hole defect routines.

Determination of double or heavy yarn and dirty yarn is completed similarly. However, instead of a lower boundary voltage value used for comparison of the pixel data generated by array 56, the upper boundary value is used to determine out of tolerance conditions. Similarly, a stack is used to store sixteen revolutions of knitting head 30. A sum of the learning mode crossing of the upper boundary is stored for use in determining an out of tolerance condition for these defects. A stack is used to keep track of sixteen revolutions of data and when the sum of the stack is greater then the stored sum plus some offset or sensitivity value for tolerance, a defect condition exists for these specific defects.

This defect determination routine executed by the digital signal processor 61 of system 60 works for fleece, jersey and non-needle out type rib material. However, for rib material with needle out, which is in effect a needle run condition, variances in the analysis must be introduced or false defects will be detected. For needle out rib material, spacing between needle outs in the material and the actual width of each needle out must be determined. If the spacing between needle outs is other than a learned distance or if the width of the needle out is larger than a learned width, a needle run condition may exist. Careful tracking of rotational position of the scanning head 50 during each revolution must be kept so that the actual location of each needle out is known during defect detection and proper width and spacing can be calculated. Under such continual monitoring of the rib location, width and spacing, effective defect detection for needle out material is accomplished.

What is claimed is:

1. A defect scanning apparatus for detection of defects in tubular knitted fabric produced on a circular knitting machine, comprising:

a circular knitting machine creating a web of tubular knit fabric;

a fiber optic scanning head attached to said circular knitting machine and reflecting light off of said tubular knit fabric and reading said reflected light;

a digital signal processor, operably connected to said circular knitting machine and said fiber optic scanning head for reading said reflected light signals from said fiber optic scanning head, said digital signal processor having instructions to determine defects in said fabric;

said fiber optic scanning head further comprised of a light emitting source, an optosensor, a first fiber optic bundle carrying light from said light emitting source to a web of material, a second fiber optic bundle reading said reflected light from said web of material to said optosensor, wherein said first fiber optic bundle is randomized between said light source and said web of material.

2. The scanning apparatus of claim 1 wherein said light emitting source on said scanning head is an incandescent lensed bulb and wherein said optosensor is a linear pixel array.

3. The scanning apparatus of claim 2 wherein said linear pixel array is a 512×1 photo-sensor array which is operably connected to said digital signal processor.

4. The scanning apparatus of claim 3 wherein said digital signal processor receives data sequentially as input from said photo-sensor array.

5. The scanning apparatus of claim 4 further comprising:

amplifier means to amplify said signals from said photosensor array;

converter means to convert said analog signal from said amplifier to a digital signal;

latch means for receiving and storing said digital signal from said converter means;

wherein said latch means is operably connected to said digital signal processor to transmit said stored digital signals to said processor.

6. The scanning apparatus of claim 1 wherein said digital signal processor is operably connected to said light emitting source to control the intensity of said light emitting source.

7. The scanning apparatus of claim 6 wherein said digital signal processor additionally dynamically adjusts said light emitting source to an optimal level by reading said reflected light signals.

8. The scanning apparatus of claim 1 wherein said digital signal processor further comprises a microprocessor, said microprocessor conducting the steps of:

reading input from an operator indicating the type of said tubular knitted fabric being produced;

loading default reflectance values for said type of tubular knitted fabric;

adjusting said default reflectance values based upon reflectance values recorded during a predetermined number of knitting revolutions;

comparing continually read reflected light signals from said fiber optic scanning head and determining the existence of defects in said tubular knitted fabric;

stopping said circular knitting machine if the existence of a defect is determined.

9. The scanning apparatus of claim 1 wherein said digital signal processor contains means to determine the existence of end out defects, hole defects, light and heavy yarn defects and needle run defects in said web of tubular knit fabric.

10. The scanning apparatus of claim 1 wherein said circular knitting machine is comprised of a knitting head, said knitting head having depending there below a circular frame member, said fiber optic scanning immediately adjacent thereto, said circular frame member additionally having a defraying bar adjacent said fiber optic scanning head.

11. An apparatus for optically monitoring a web of knitted material, comprising:

a circular knitting machine having a knitting head, an upper and a lower circular support frame member depending below said knitting head and a vertical support member extending upward therethrough;

a fiber optic scanning head attached to said first circular support frame such that said head is directly adjacent to the interior of said web of knitted material;

a digital signal processing system operably connected to said knitting machine;

a retention bracket extending downward from said knitting head and securely affixed to said upper circular support member;

said vertical support member extending through a central hub on said upper circular support frame member, said hub additionally having an attachment arm extending outward therefrom, said attachment arm affixed to said fiber optic scanning bead such that said scanning head is adjacent to the periphery of said upper circular support frame member;

wherein said lower circular support frame member and said vertical support member rotate with said web of knitted material and further wherein said upper circular support member remains stationary.

12. The apparatus of claim 11 further comprising a defraying bar depending below said upper circular support member and adjacent to said scanning head.

13. The apparatus of claim 11 wherein said upper circular support frame member has a diameter which is less than the diameter of said lower circular support frame member.

14. The apparatus of claim 11 wherein said digital signal processing system is comprised of a digital signal processor, a first and a second 8-bit latch, an analog to digital converter, an amplifier and a pixel linear array, said digital signal processor further operably connected to a light emitting source and a voltage regular and digital potentiometer.

15. The digital signal processor of claim 14 wherein said processor is further comprised of a communications port for receiving data from an external source, said processor further operably connected to said knitting machine and receiving timing signals therefrom.

16. The digital signal processor of claim 14 further comprising read only memory containing instructions for detecting defects in said web of knitted material, said instructions comprising:

> adjusting said light emitting source to an optimal voltage level for detecting defects in said web;
>
> learning upper and lower boundary values for each of the pixels in said pixel linear array;
>
> calculating a minimum and maximum average voltage scan for said pixel linear array;
>
> detecting defects in said web, said defects including holes, needle runs, end outs, light yarn, dirty yarn and double yarn.

17. The apparatus of claim 11 wherein said digital signal processor further comprises:

> means to dynamically adjust a light emitting source incorporated within said fiber optic scanning head;
>
> means to learn boundary voltage readings for each pixel in said scanning head;
>
> means to determine the existence of hole defects, needle run defects, light yarn, heavy yarn or needle run conditions.

18. A defect detection apparatus for a circular knitting machine, comprising:

> a circular knitting machine, said knitting machine having a knitting head supported on a frame and a support frame member depending therebelow;
>
> a scanning head securely affixed to said support fame member, said scanning head having a light source and a light detection mechanism;
>
> a digital signal processor operably connected to said scanning head and said circular knitting machine;
>
> said digital signal processor further having on board memory having instructions for the steps of: (1) a lamp brightness routine, said lamp brightness adjustment routine setting and adjusting said light source to an optimal value based upon stored values; (2) a first learning routine to determine boundary values for detection of holes and needle runs; and (3) a second learning routine for creation of a data stack for detection of yarn defects.

* * * * *

UNITED STATES PATENT AND TRADEMARK OFFICE
CERTIFICATE OF CORRECTION

PATENT NO.   : 6,219,136 B1
DATED        : April 17, 2001
INVENTOR(S)  : Kuo et al.

It is certified that error appears in the above-identified patent and that said Letters Patent is hereby corrected as shown below:

Column 1,
Line 37, change "characterized" to -- characterize --;
Line 53, after "of", delete "a";

Column 3,
Line 6, change "than" to -- then --;

Column 4,
Line 17, change "intention" to -- invention --;
Line 47, change "take-up" to -- take up --;
Line 67, after "digital" insert -- signal processing --;

Column 11,
Line 23, change "60" to -- 61 --;

Column 14,
Line 67, change "regular" to -- regulator --;

Column 16,
Line 10, change "fame" to -- frame --.

Signed and Sealed this

Twenty-fifth Day of June, 2002

Attest:

Attesting Officer

JAMES E. ROGAN
*Director of the United States Patent and Trademark Office*